US006288109B1

United States Patent
Chatterjee et al.

(10) Patent No.: US 6,288,109 B1
(45) Date of Patent: Sep. 11, 2001

(54) PYRANONES, METHOD FOR THE PRODUCTION AND USE THEREOF

(75) Inventors: Shyam Sunder Chatterjee; Hermann Hauer, both of Karlsruhe (DE)

(73) Assignee: Dr. Willmar Schwabe GmbH & Co., Karlsruhe (DE)

( * ) Notice: Subject to any disclaimer, the term of this patent is extended or adjusted under 35 U.S.C. 154(b) by 0 days.

(21) Appl. No.: 09/554,382

(22) PCT Filed: Nov. 12, 1998

(86) PCT No.: PCT/EP98/07241

§ 371 Date: May 12, 2000

§ 102(e) Date: May 12, 2000

(87) PCT Pub. No.: WO99/25716

PCT Pub. Date: May 27, 1999

(30) Foreign Application Priority Data

Nov. 14, 1997 (DE) .............................. 197 50 623

(51) Int. Cl.[7] .................................................. A61K 31/35
(52) U.S. Cl. .............................. 514/460; 549/292
(58) Field of Search .............................. 549/292; 514/460

(56) References Cited

FOREIGN PATENT DOCUMENTS 1277223    9/1968  (DE) .
1279683   10/1968  (DE) .

OTHER PUBLICATIONS

Meyer, H.J., Kretzschmar, R.: Untersuchungen uber Beziehungen zwischen Molekularstruktur und pharmakologischer Wirkung C6–arylsubstituierter 4–Methoxy–a–pyrone vom Typ der Kawa–Pyrone. Arzneim.—Forsch. 19, 1969, S. 617–623; (Summary in English).

Alhakimi, Gamil, et al.: Polymides by Diels–Alder polyaddition of a–pyrones. Macromol. Chem. Phys. 195, 1994, S. 1569–1576.

*Primary Examiner*—Amelia Owens
(74) *Attorney, Agent, or Firm*—Frost Brown Todd LLC

(57) ABSTRACT

The invention relates to a novel 2H-1-pyran-2-ones of general formula (I),

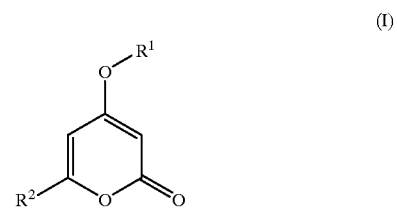

wherein $R^1$ represents an alkyl radical with 2–5 C atoms, a cycloakyl radical with 4–6 C atoms, a cycloalkyl radical with 4–8 C atoms or an alkoxy alkyl radical with a total of 3–5 C atoms and $R^2$ represents a 2-(3, 4-methylene dioxyphenyl) radical or a 2-phenyl ethenyl radical substituted with $R^3$, $R^4$ and $R^5$ in positions 3, 4 and 5, whereby independently from each other $R^3$ and $R^5$ represent methoxy or ethoxy and $R^4$ is a straight chain or branched alkoxy radical with 1–5 C atoms, an alkenyl radical with 3–5 C atoms, a cycloalkoxy radical with 4–6 C atoms, a cycloalkyl radical with 4–8 C atoms or an alkoxy alkoxy radical with a total of 3–5 C atoms. The invention also relates to a method for producing said compunds in addition to novel untermediate products and to a method for the production thereof. The novel pyranone derivatives have an anticonvulsive and/or anti-epileptic efect in addition to a neuroprotective effect or act against neurodegenerate diseases. The invention further relates to medicaments containing these compounds.

12 Claims, No Drawings

PYRANONES, METHOD FOR THE PRODUCTION AND USE THEREOF

The invention relates to pyranones, the basic structure of which can be derived from lactones which occur in the plant *Piper methysticum*, methods of preparing the said compounds, including the resulting intermediate products, and medicaments which contain the said compounds.

The use of kava (*Piper methystium*) extracts for the therapy of anxiety and similar psychological diseases has been known for a long time. It is likewise known that the socalled kava pyrones (kawain, dihydrokawain, methysticin, dihydromethysticin and yangonin) form the active component of such extracts. Numerous pharmacological investigations have demonstrated the various biological effects of pure substances of this type as well as their anti-convulsive and neuro-protective properties [cf. R. Kretzschmar et al., Arch. Int. Pharmacodyn. Ther. 177, pp. 261 subsequ. (1969) and C. Backhauss et al., Europ. J. Pharmacol. 215, pp. 265 subsequ. (1992)]. Until now, however, the practical therapeutic application of kava pyrones as anti-epileptics or for treating neuro-degenerative diseases has not been known. We have found that the known kava pyrones are unsuitable for the therapy of epilepsy and neuro-degenerative diseases, since the active duration of these substances after oral administration is very short, and in addition the oral bio-availability of many of these natural substances is inadequate. Furthermore, a serious obstacle to the industrial production of suitable medicaments is the fact that the isolation of new natural substances from the kava root or other plants is very complicated, which would make therapy with such compounds very expensive and thus uneconomic. In addition, the industrial exploitation is subject to the problem that the natural substances are optically active, whereas racemates are involved in the case of the previously known derivatives of kava lactones which are produced by simpler synthesis. Since the effects of kava lactones depend upon their enantiomeric form, only those kava lactones which are synthesized stereo-selectively can be used for therapeutic purposes.

Until now, however, no stereo-specific synthesis methods of this type which can be applied commercially are known for this class of substances.

The object of the invention is therefore to provide novel pyranone derivatives which have a sufficiently strong anti-convulsive effect when administered orally and have an active duration of several hours and can be used as pharmaceutical active ingredients, in particular in the therapy of diseases of the central nervous system.

This object is attained by the preparation of the compounds and methods according to the invention as well as by the use of the said compounds as medicaments which have an anti-convulsive and anti-epileptic effect [when administered] orally.

The subject of the invention is thus:

2H-1-pyran-2-ones of the general formula I,

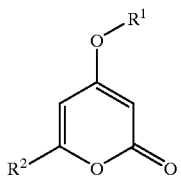

(I)

in which

R$^1$ represents an alkyl radical with from 2 to 5 C atoms, a cycloalkyl radical with from 4 to 6 C atoms, a cycloalkyl alkyl radical with from 4 to 8 C atoms or an alkoxyalkyl radical with altogether 3 to 5 C atoms, and R$^2$ represents a 2-(3,4-methylene dioxyphenyl)ethyl radical or a 2-phenyl ethenyl radical substituted with R$^3$, R$^4$ and R$^5$ in positions 3, 4 and 5 on the benzene ring, wherein, independently of one another, R$^3$ and R$^5$ are methoxy or ethoxy, and R$^4$ is a straight-chain or branched alkoxy radical with from 1 to 5 C atoms, an alkenyloxy radical with from 3 to 5 C atoms, a cycloalkoxy radical with from 4 to 6 C atoms, a cycloalkyl alkoxy radical with from 4 to 8 C atoms or an alkoxy alkoxy radical with altogether 3 to 5 C atoms.

The compounds according to the invention are novel.

The compound 4-methoxy-6-[2-(3,4-methylene dioxyphenyl)ethyl]-2H-pyran-2-one is known (H. J. Meyer and R. Kretzschmar, *Arzneim.-Forsch.* [Medicinal Research] 19, 617 (1969)) and its moderately anti-convulsive effect with i.v. administration. The naturally occurring kava lactones are also known—methysticin (E-(+)-6-[2-(1,3-benzo-dioxol-5-yl)ethenyl]-5,6-dihydro-4-methoxy-2H-pyran-2-one), dihydromethysticin ((+)-6-[2-(1,3-benzodioxol-5-yl)ethyl]-5,6-dihydro-4-methoxy-2H-pyran-2-one), kawain (E-(+)-5,6-dihydro-4-methoxy-6-(2-phenylethenyl)-2H-pyran-2-one), dihydrokawain ((+)-5,6-dihydro-4-methoxy-6-(2-phenylethyl)-2H-pyran-2-one), yangonin (E-4-methoxy-6-[2-(4-methoxyphenyl)ethenyl]-2H-pyran-2-one) and desmethoxy-yangonin (E-4-meth-oxy-6(2-phenylethenyl)-2H-pyran-2-one), as well as their anti-convulsive effect with oral administration (R. Kretzschmar and H. J. Meyer, Arch. Int. Pharmacodyn. Ther. 177, 261 (1969)). These compounds are hardly effective, however, in the MES test after 3 h.

With respect to this prior art, it was surprising and in no way predictable to the person skilled in the art that the compounds of the general formula I according to the invention have a good anti-convulsive and anti-epileptic effect which lasts over several hours with oral administration, and so in many cases they have a longer active duration than the kava lactones occurring naturally. An important advantage achieved according to the invention is that it is possible to dispense with the complicated isolation of natural substances and to use simple processes of synthesis which do not require any stereoselective process performance, since the novel substances are achiral, i.e. do not have any asymmetric centres.

Compounds of the general formula I preferred according to the invention are those in which R$^1$ represents an alkyl radical with from 2 to 5 C atoms, a cyclopropylmethyl radical or a methoxyethyl radical, and R$^2$ represents a 2-(3,4-methylene dioxyphenyl)ethyl radical or a 2-phenyl ethenyl radical substituted with R$^3$, R$^4$ and R$^5$ in positions 3, 4 and 5 on the benzene ring, wherein, independently of one another, R$^3$ and R$^5$ are methoxy, and R$^4$ is a straight-chain or branched alkoxy radical with from 1 to 5 C atoms, an allyloxy radical, a cyclopentyloxy radical, a cyclopropyl methoxy radical or a methoxyethoxy radical.

In the process according to the invention for preparing the compounds of the general formula I, in the case of R$^2$=2-(3,4-methylene dioxyphenyl)ethyl a compound of the general formula II,

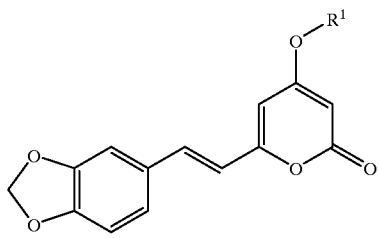

(II)

in which R¹ has the value indicated above, is reacted with hydrogen in the presence of a catalyst.

Alternatively, 6-[2-(1,3-benzodioxol-5-yl)ethyl]-4-hydroxy-2H-pyran-2-one can also be alkylated with R¹X, in which R¹ has the value indicated above.

The compounds of the general formula I, in which $R^2$ is a 2-phenyl ethenyl radical substituted with $R^3$, $R^4$ and $R^5$ in positions 3, 4 and 5 on the benzene ring, and the compounds of the general formula II are prepared by condensation of the pyranone of the general formula III—substituted accordingly with R¹—with piperonal (3,4-methylene dioxybenzaldehyde) or with a benzaldehyde of the general formula IV substituted with $R^3$, $R^4$ and $R^5$ in positions 3, 4 and 5, in which $R^3$, R4 and $R^5$ have the values indicated above.

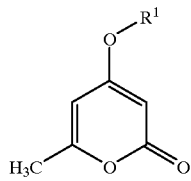

(III)

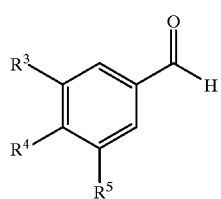

(IV)

The compounds of the general formula III are obtained by alkylation of 4-hydroxy-6-methyl-2H-pyran-2-one with R¹X.

The compounds of the general formula IV are obtained by O-alkylation of a benzaldehyde substituted accordingly with $R^3$, $R^4$ and $R^5$ and in which one or two of the radicals $R^3$ to $R^5$ have the value indicated above and the remaining radicals $R^3$ to $R^5$ are hydroxy.

The intermediate products II and III, insofar as they are novel, likewise constitute the subject matter of the invention.

In addition, subjects of the invention are orally effective medicaments which contain one or more of the compounds of the general formula I according to the invention as the active ingredient and optionally, in addition, pharmacologically inert adjuvants, such as for example water, vegetable oils, polyethylene glycols, glycerin esters, gelatins, carbohydrates such as lactose or starch, magnesium stereate, talc, Vaseline®, preservatives, wetting agents, emulsifiers, physiologically harmless salts, buffer agents, dyes, flavouring and aromatizing substances. The choice of the accompanying substances depends upon whether the medicaments are to be applied orally in the form of tablets, dragées, in a liquid form or in the form of sprays. The compounds according to the invention can also be administered in a mixture with other known active ingredients. The oral effectiveness of these medicaments does not exclude the active ingredients and medicaments according to the invention from also being effective in a non-oral application.

The compounds according to the invention, the methods of preparing them and the pharmacological test results are described in greater detail in the following Examples.

The abbreviations used in the following text signify: TBME=tert.-butyl methyl ether, PE=petroleum ether, DMSO=dimethyl sulfoxide and DMF=N,N-dimethyl formamide. "Rotating-in" is understood to be drawing off solvent (residues) until dry by using a rotary evaporator.

I. Examples 1 to 5 for end Products of the General Formula I in which $R^2$ Represents a 2-(3,4-methylene dioxyphenyl)ethyl Radical In order to prepare the compounds described in greater detail in the following Examples 1 to 5, the following methods have been used:

Method A:

The 4-alkoxy-6-[2-(3,4-methylene dioxyphenyl)ethenyl]-2H-pyran-2-one of the general formula II substituted appropriately with R¹ is hydrogenated in a chloro-form/methanol-⅔-mixture with the addition of from 9 to 30% by weight of palladium (5% on carbon) for 2 to 15 h at an initial pressure of from 7 to 8 bar of hydrogen and room temperature. The reaction mixture is filtered and the solvent is removed in a vacuum. The residue is cleaned by chromatography and/or re-crystallization.

Method B:

A solution of 1·0 equivalent 6-[2-(1,3-benzodioxol-5-yl)ethyl-]4-hydroxy-2H-pyran-2-one (Example 28) in DMF is added dropwise to a suspension of sodium hydride (60% in white oil) in DMF at 0° C. Stirring is carried out for 1·5 h at 0° C., 1·1 equivalents of bromoalkane R¹Br are added dropwise and stirring is carried out for 50 h at 25° C. The excess alkylating agent is broken down with ammonia solution (32% in water) and the solvent is removed in a vacuum. The residue is absorbed in ethyl acetate, the ethyl acetate solution is washed with water, dried (sodium sulphate), filtered and rotated-in. The raw product is chromatographed over silica gel and re-crystallized.

| Exam. No. | Name | Formula | Meth. | St. mat. Exam. | Yield [%] | m.p. [° C.] (solvent) |
|---|---|---|---|---|---|---|
| 1 | 6-[2-(1,3-benzodioxol-5-yl)ethyl]-4-ethoxy-2H-pyran-2-one | C16H16O5 | A | 28 | 75 | 139.5–140.5 TBME/ethanol |
| 2 | 6-[2-(1,3-benzodioxol-5-yl)ethyl]-4-(1-methyl-ethoxy)-2H-pyran-2-one | C17H18O5 | A | 29 | 67 | 106–108 TBME/ethylacetate |

-continued

| Exam. No. | Name | Formula | Meth. | St. mat. Exam. | Yield [%] | m.p. [° C.] (solvent) |
|---|---|---|---|---|---|---|
| 3 | 6-[2-(1,3-benzodioxol-5-yl)ethyl]-4-propyloxy-2H-pyran-2-one | C17H18O5 | B | 32 | 72 | 98 TBME/PE |
| 4 | 6-[2-(1,3-benzodioxol-5-yl)ethyl]-4-butyloxy-2H-pyran-2-one | C18H20O5 | A | 30 | 71 | 84.5–85.5 TBME/PE |
| 5 | 6-[2-(1,3-benzodioxol-5-yl)ethyl]-4-(2-methoxy-ethoxy)-2H-pyran-2-one | C17H18O6 | A | 31 | 72 | 86–87 TBME/PE |

II. Examples 6 to 27 for end Products of the General Formula I, in which $R^2$ Represents a 2-phenyl Ethenyl Radical Substituted with $R^3$, $R^4$ and $R^5$ In order to prepare the compounds described in greater detail in the following Examples 6 to 27, the following method has been used:

Method C:

Equimolar quantities of the 4-alkoxy-6-methyl-2H-pyran-2-one of the general formula III substituted appropriately with $R^1$ and the benzaldehyde of the general formula IV substituted appropriately with $R^3$, $R^4$ and $R^5$ are dissolved in DMSO and are first mixed at 15° C. to room temperature with 0·1 equivalents of tetraethyl ammonium hydroxide solution (40% in water), then (30 min to 3 h later) with 0·5 equivalents of potassium hydroxide (50% in water) and are stirred from 15 to 20 h under nitrogen at room temperature. The reaction mixture is diluted with water or diluted hydrochloric acid, the precipitated product is obtained by filtration or extraction with ethyl acetate or TBME, and is chromatographed over silica gel and/or re-crystallized.

| Exam. No. | Name | Formula | Meth. | St. mat. Exam. | Yield [%] | m.p. [° C.] (solvent) |
|---|---|---|---|---|---|---|
| 6 | E-4-ethoxy-6-[2-(3,4,5-trimethoxyphenyl)ethenyl]-2H-pyran-2-one | C18H20O6 | C | a) | 26 | 148–150 TBME/ethanol |
| 7 | E-4-(1-methylethoxy)-6-[2-(3,4,5-trimethoxyphenyl)-ethenyl]-2H-pyran-2-one | C19H22O6 | C | 33 | 39 | 94–95 TBME/PE |
| 8 | E-4-propoxy-6-[2-(3,4,5-trimethoxyphenyl)ethenyl]-2H-pyran-2-one | C19H22O6 | C | 34 | 28 | 117–118 TBME/ethanol |
| 9 | E-4-(2-metylpropoxy)-6-[2-(3,4,5-trimethoxy-phenyl)ethenyl]-2H-pyran-2-one | C20H24O6 | C | 35 | 27 | 130–131 TBME/ethanol |
| 10 | E-4-(cyclopropylmethoxy)-6-[2-(3,4,5-trimethoxy-phenyl)ethenyl]-2H-pyran-2-one | C20H22O6 | C | 37 | 39 | 148.5–149 TBME/ethanol |
| 11 | E-4-(2-methoxyethoxy)-6-[2-(3,4,5-trimethoxy-phenyl)ethenyl]-2H-pyran-2-one | C19H22O7 | C | 38 | 34 | 145.5–146.5 PE/ethanol |
| 12 | E-6-{2-[4-ethoxy-3,5-dimethoxyphenyl]ethenyl}-4-(2-methoxyethoxy)-2H-pyran-2-one | C20H24O7 | C | 38 Ald #172 | 33 | 132–133 PE/ethylacetate |
| 13 | E-6-[2-(3,5-dimethoxy-4-propoxyphenyl)ethenyl]-4-(2-methoxyethoxy)-2H-pyran-2-one | C21H26O7 | C | 38 Ald #185 | 27 | 120–121 TBME |
| 14 | E-6-{2-[3,5-dimethoxy-4-(2-methylpropoxy)phenyl]-ethenyl}-4-(2-methoxy-ethoxy)-2H-pyran-2-one | C22H28O7 | C | 38 40 | 26 | 133–133.5 TBME/PE |
| 15 | E-6-{2-(4-butoxy-3,5-dimethoxyphenyl]ethenyl}-4-(2-methoxyethoxy)-2H-pyran-2-one | C22H28O7 | C | 38 Ald #193 | 25 | 123.5–124 TBME |
| 16 | E-6-[2-(4-ethoxy-3,5-dimethoxyphenyl)etheneyl]-4-(1-methylethoxy)-2H-pyran-2-one | C20H24O6 | C | 33 Ald #172 | 35 | 113.5–114 TBME/PE |

-continued

| Exam. No. | Name | Formula | Meth. | St. mat. Exam. | Yield [%] | m.p. [° C.] (solvent) |
|---|---|---|---|---|---|---|
| 17 | E-4-(1-methylethoxy-6-[2-(3,5-dimethoxy-4-propoxy-phenyl)ethenyl]-2H-pyran-2-one | C21H26O6 | C | 33 Ald #185 | 35 | 112–112.5 PE/ethanol/TBME |
| 18 | (+−)-E-6{2-[3,5-dimethoxy-4-(1-methylpropoxy)-phenyl]ethenyl}-4-(1-methylethoxy)-2H-pyran-2-one | C22H28O6 | C | 33 39 | 28 | 103–103.5 TBME/PE |
| 19 | 6-{2-[3,5-dimethoxy-4-(2-methylpropoxy)phenyl]-ethenyl}-4-(1-methyl-ethoxy)-2H-pyran-2-one | C22H28O6 | C | 33 40 | 32 | 129.5–130.5 PE/TBME |
| 20 | E-6-[2-(4-butoxy-3,5-dimethoxyphenyl)ethenyl]-4-(1-methylethoxy)-2H-pyran-2-one | C22H28O6 | C | 33 Ald #193 | 40 | 93–94 PE/isopropanol |
| 21 | E-6-[2-(3,5-dimethoxy-4-pentyloxyphenyl)ethenyl]-4-(1-methylethoxy)-2H-pyran-2-one | C23H30O6 | C | 33 41 | 33 | 105.5–106.5 PE/isopropanol |
| 22 | E-6-{2-[4-(cyclopropyl-methoxy)-3,5-dimethoxy-phenyl]ethenyl}-4-(1-methylethoxy)-2H-pyran-2-one | C22H26O6 | C | 33 42 | 33 | 122.5–123 ethanol/TBME/PE |
| 23 | E-6-{2-[4-(cyclopentyl-oxy)-3,5-dimethoxy-phenyl]ethenyl}-4-(1-methylethoxy)-2H-pyran-2-one | C223H28O6 | C | 33 43 | 33 | 107–107.5 ethanol/TBME/PE |
| 24 | E-6-{2-[3,5-dimethoxy-4-(2-propenyloxy)phenyl]-ethenyl}-4-(1-methyl-ethoxy)-2H-pyran-2-one | C21H24O6 | C | 33 Ald #196 | 22 | 116–116.5 TBME/PE/ethanol |
| 25 | E-6-{3-[3,5-dimethoxy-4-(2-methoxyethoxy)phenyl]-ethenyl}-4-(1-methyl-ethoxy)-2H-pyran-2-one | C21H26O7 | C | 33 Ald #203 | 40 | 88.5–89 TBME/PE |
| 26 | E-6-[2-(4-ethoxy-3,5-dimethoxyphenyl)ethenyl]-4-propoxy-2H-pyran-2-one | C20H24O6 | C | 34 Ald #172 | 19 | 132.5–133 TBME/PE/ethanol |
| 27 | E-6-[2-(3-ethoxy-4,5-dimethoxyphenyl)ethenyl]-4-(1-methylethoxy)-2H-pyran-2-one | C20H24O6 | C | 33 Ald #243 | 29 | 120.5–121 TBME | a) 6-methyl-4-ethoxy-2H-pyran-2-one (known)

The aldehydes used as starting materials in Examples 12, 13, 15, 16, 17, 20, 24, 25, 26 and 27 are the following known compounds:

Ald. #172: 4-ethoxy-3,5-dimethoxy-benzaldehyde
Ald. #185: 3,5-dimethoxy-4-propoxy-benzaldehyde
Ald. #193: 4-butoxy-3,5-dimethoxy-benzaldehyde
Ald. #196: 3,5-dimethoxy-4-(2-propenyloxy)-benzaldehyde
Ald. #203: 3,5-dimethoxy-4-(2-methoxyethoxy)-benzaldehyde
Ald. #243: 3-ethoxy-4,5-dimethoxy-benzaldehyde III. Examples 28 to 31, for Intermediate Products of the General Formula II In order to prepare the compounds described in greater detail in the following Examples 28 to 31, the method C described above under II has been used, but with piperonal as the benzaldehyde component:

| Exam. No. | Name | Formula | Meth. | St. mat. Exam. | Yield [%] | m.p. [° C.] (solvent) |
|---|---|---|---|---|---|---|
| 28 | E-6-[2-(1,3-benzodioxol-5-yl)-ethenyl]-4-ethoxy-2H-pyran-2-one | C16H14O5 | C | a) | 61 | 204.5–205 acetone/ethanol/TBME |
| 29 | E-6-[2-(1,3-benzodioxol-5-yl)-ethenyl]-4-(1-methylethoxy)-2H-pyran-2-one | C17H16O5 | C | 33 | 51 | 155–157 acetone |

-continued

| Exam. No. | Name | Formula | Meth. | St. mat. Exam. | Yield [%] | m.p. [° C.] (solvent) |
|---|---|---|---|---|---|---|
| 30 | E-6-[2-(1,3-benzodioxol-5-yl)-ethenyl]-4-butyloxy-2H-pyran-2-one | C18H18O5 | C | 36 | 37 | 130–131 ethanol/TBME |
| 31 | E-6-[2-(1,3-benzodioxol-5-yl)-ethenyl]-4-(2-methoxy-ethoxy)-2H-pyran-2-one | C17H16O6 | C | 38 | 37 | 143.5–144.5 TBME/PE/ ethanol |

[a)] 6-methyl-4-ethoxy-2H-pyran-2-one (known)

IV. Example 32: 6-[2-(1,3-benzodioxol-5-yl)ethyl]-4-hydroxy-2H-pyran-2-one 6-methyl-4-(phenylmethoxy)-2H-pyran-2-one (known) was reacted with piperonal in accordance with Method C described above under II to form E-6-[2-(1,3-benzodioxol-5-yl)ethenyl]-4-(phenylmethoxy)-2H-pyran-2-one: C21H16O5; yield 39%, melting point 150 to 152° C. (acetone). This condensation product was hydrogenated in accordance with Method A described above under I. For cleaning purposes the product was taken up in ethyl acetate, was extracted therefrom with 2 N potassium hydroxide solution and was precipitated from the latter by acidification: C14H12O5; yield 67%, melting point 200 to 201° C. (isopropanol/water).

V. Examples 33 to 38 for Intermediate Products of the General Formula III

In order to prepare the compounds described in greater detail in the following Examples 33 to 38, the following methods were used:

Method D:

4-hydroxy-6-methyl-2H-pyran-2-one, 1·5 equivalents of the appropriately substituted alkyl bromide $R^1Br$, 1·5 equivalents of potassium carbonate and 0·2 equivalents of potassium iodide are stirred in DMF for 30 to 40 h under nitrogen at 80° C. Excess alkylating agent is broken down with ammonia solution, filtering is carried out, the filtrate is rotated in, taken up in ethyl acetate, filtered once more or washed with water and dried with sodium sulphate and rotated in. The residue is re-crystallized.

Method E:

A solution of 4-hydroxy-6-methyl-2H-pyran-2-one in DMF is added dropwise at from 0 to 15° C. to one equivalent of sodium hydride (60% in white oil) in DMF and is stirred for 1 to 2 h at from 0° C. to room temperature. From 1·1 to 1·25 equivalents of the appropriately substituted alkyl halide $R^1Cl$, $R^1Br$ or $R^1I$ in DMF and optionally up to 0·1 equivalents of potassium iodide are added and are stirred for 15 to 20 h at from room temperature to 100° C. under nitrogen. Excess alkylating agent is optionally broken down with ammonia solution. The reaction mixture is rotated in, the residue is taken up in ethyl acetate, is optionally washed with sodium hydroxide solution and with water, and is dried with sodium sulphate and rotated in. The crude product is re-crystallized or cleaned by column chromatography and optionally distilled in a vacuum.

| Exam. No. | Name | Formula | Meth. | Yield [%] | m.p. [° C.] (solvent) |
|---|---|---|---|---|---|
| 33 | 6-methyl-4-(1-methylethoxy)-2H-pyran-2-one | C9H12O3 | D | 79 | 55–56 TBME/PE |
| 34 | 6-methyl-4-propoxy-2H-pyran-2-one | C9H12O3 | E | 78 | oil (b.p. 100–102/ 0.03 mbar) |
| 35 | 6-methyl-4-(2-methylpropoxy)-2H-pyran-2-one | C10H14O3 | E | 47 | oil |
| 36 | 4-butyloxy-6-methyl-2H-pyran-2-one | C10H14O3 | E | 87 | oil |
| 37 | 4-(cyclopropylmethoxy)-6-methyl-2H-pyran-2-one | C10H12O3 | E | 62 | 70–70.5 PE/TBME |
| 38 | 4-(2-methoxyethoxy)-6-methyl-2H-pyran-2-one | C9H12O4 | E | 63 | 77.5–78.5 TBME/ PE |

VI. Examples 39 to 43 for Intermediate Products of the General Formula IV

In order to prepare the compounds described in greater detail in the following Examples 39 to 43, the following method was used:

Method F:

4-hydroxy-3,5-dimethoxybenzaldehyde, 2 equivalents of the appropriately substituted alkyl halide $R^4Cl$, $R^4Br$ or $R^4I$, from 1·5 to 2 equivalents of potassium carbonate or potassium hydroxide and optionally 0·2 equivalents of potassium iodide are stirred in DMF for 15 to 60 h under nitrogen at from 75 to 90° C. Filtering takes place, the filtrate is rotated in, taken up in ethyl acetate, washed with water, dried over sodium sulphate and rotated in. The residue is optionally cleaned by means of column chromatography and/or re-crystallization.

| Exam. No. | Name | Formula | Meth. | Yield [%] | m.p. [° C.] (solvent) |
|---|---|---|---|---|---|
| 39 | (+−)-3,5-dimethoxy-4(1-methylpropoxy)-benzaldehyde | C13H18O4 | F | 35 | oil |
| 40 | 3,5-dimethoxy-4-(2-methyl-propoxy)-benzaldehyde | C13H18O4 | F | 58 | oil |
| 41 | 3,5-dimethoxy-4-pentyloxy-benzaldehye | C14H20O4 | F | 91 | ~28–30 PE/TBME |
| 42 | 4-(cyclopropylmethoxy)-3,5-dimethoxy-benzaldehyde | C13H16O4 | F | 86 | 56.5–57 PE/TBME |
| 43 | 4-cyclopentyloxy-3,5-dimethoxy-benzaldehyde | C14H18O4 | F | 73 | 47.5–48 isopropanol/water |

Pharmacological Investigations

The methods described by E. A. Swinyard et al. (J. Pharmacol. Exp. Ther. 106, 319 (1952)) and by L. A. Woodbury et al. (Arch. int. Pharmacodyn. 92, 97 (1952)) were used to determine the anti-convulsive/anti-epileptic activity of the substances according to the invention. An alternating current of 50 Hz and 50 mA was applied for 0·2 sec (HSE shock-stimulus appliance, Type 207) to male mice (NMRI) with a body weight of from 20 to 25 g by way of corneal electrodes. The maximum electric shock (MES) convulsion consists of a tonic stretching of the rear extremities, clonic twitching and a loss of consciousness. The inhibition of extensor convulsion by the substances according to the invention is considered to be a criterion of effectiveness. The mice had free access to food and water before the experiments. The test substances were applied orally as a suspension in 0·2% agar per os by a swallowed probe; the control animals were given equivalent amounts of agar. The test for the protective effect against MES was carried out 1 hour and 3 hours after application.

The results of the MES test with dosages of 100 mg of the compounds according to the invention per kg of body weight are listed in the table set out below. The percentage of those animals, which were 100% protected against extensor convulsion in the MES test is indicated as a percentage effect.

During the experiments described above, the animals were observed within the entire duration of the tests for signs of changes in behaviour and neurotoxicity caused by the substances (motility, muscle tone, frequency of breathing, body temperature and general behaviour). No side effects could be observed in any of the substances according to the invention tested.

| Exam. No. | Dose [mg/kg] | No. of animals | protection after 1 h [%] | protection after 3 h [%] |
|---|---|---|---|---|
| 1 | 100 | 8 | 37.5 | 37.5 |
| 2 | 100 | 8 | 25 | 50 |
| 3 | 100 | 8 | 100 | 87.5 |
| 4 | 100 | 8 | 87.5 | 100 |
| 5 | 100 | 8 | 62.5 | 75 |
| 6 | 100 | 8 | 100 | 50 |
| 7 | 100 | 8 | 100 | 75 |
| 8 | 100 | 8 | 87.5 | 75 |
| 9 | 100 | 8 | 25 | 62.5 |
| 10 | 100 | 8 | 37.5 | 62.5 |
| 11 | 100 | 8 | 87.5 | 50 |
| 12 | 100 | 8 | 100 | 100 |
| 13 | 100 | 8 | 100 | 100 |
| 14 | 100 | 8 | 75 | 87.5 |
| 15 | 100 | 8 | 100 | 100 |
| 16 | 100 | 8 | 100 | 100 |
|  | 50 | 8 | 75 | 75 |
| 17 | 100 | 8 | 100 | 100 |
|  | 50 | 10 | 80 | 100 |
| 18 | 100 | 8 | 100 | 100 |
| 19 | 100 | 8 | 100 | 100 |
| 20 | 100 | 8 | 100 | 100 |
| 21 | 100 | 8 | 50 | 50 |
| 22 | 100 | 8 | 100 | 75 |
| 23 | 100 | 8 | 62.5 | 25 |
| 24 | 100 | 8 | 87.5 | 87.5 |
| 25 | 100 | 8 | 87.5 | 87.5 |
| 26 | 100 | 8 | 62.5 | 87.5 |
| 27 | 100 | 8 | 87.5 | 62.5 |

The data of Kretzschmar and Meyer are set out below (comparison):

| | | | | |
|---|---|---|---|---|
| methysticin | 70 | 10–45 | 80 | 17.5 |
| dihydromethysticin | 70 | 10–45 | 55 | <10 |
| kawain | 150 | 10–45 | 0 | 0 |
| dihydrokawain | 150 | 10–45 | 0 | 0 |
| yangonin | 750 | 10–45 | 20 | 40 |
| desmothoxy yangonin | 400 | 10–45 | 50 (at maximum effectiveness after 20 min) | |

Examples of the Production of Pharmaceutical Preparations of the Substances According to the Invention A. Tablets:

In order to produce tablets which contain from 5 to 250 mg of active ingedient depending upon the desired effective strength, the following are required:

| | |
|---|---|
| substance according to the invention | from 200 to 5,000 g |
| cellulose powder | 2,000 g |
| maize starch | 1,200 g |
| colloidal silicic acid | 80 g |
| magnesium stearate | 20 g |
| lactose | ad 10,000 g |

The active ingredient is optionally ground, is mixed homogeneously with the adjuvants and is pressed in the usual manner to form tablets each of 250 mg in weight and 9 mm in diameter. In the case of dosages of over 125 mg, tablets each of 500 mg in weight and 11 mm in diameter are pressed. If desired, the tablets are provided with a film coating.

B. Capsules:

In order to produce capsules which contain from 5 to 250 mg of active ingedient depending upon the desired effective strength, the following are required:

| substance according to the invention | from 500 to 12,500 g |
|---|---|
| maize starch | 2,000 g |
| colloidal silicic acid | 300 g |
| magnesium stearate | 50 g |
| cellulose powder | ad 20,000 g |

The finely ground substances are mixed homogeneously and are filled into hard gelatine capsules of size 2 in the quantity of 200 mg per capsule, or, in the case of dosages of over 125 mg, into hard gelatine capsules of size 0 in the quantity of 400 mg per capsule.

What is claimed is:

1. A 2H-1-pyran-2-one of formula I,

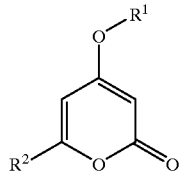

(I)

wherein
R$^1$ represents an alkyl radical with from 2 to 5 C atoms, a cycloalkyl radical with from 4 to 6 C atoms, a cycloalkyl alkyl radical with from 4 to 8 C atoms or an alkoxyalkyl radical with altogether 3 to 5 C atoms, and
R$^2$ represents a 2-(3,4-methylene dioxyphenyl)ethyl radical or a 2-phenyl ethenyl radical substituted with R$^3$, R$^4$ and R$^5$ in positions 3, 4 and 5 on the benzene ring,
and wherein, independently of one another,
R$^3$ and R$^5$ are methoxy or ethoxy, and
R$^4$ is a straight-chain or branched alkoxy radical with from 1 to 5 C atoms, an alkenyloxy radical with from 3 to 5 C atoms, a cycloalkoxy radical with from 4 to 6 C atoms, a cycloalkyl alkoxy radical with from 4 to 8 C atoms or an alkoxy alkoxy radical with altogether 3 to 5 C atoms.

2. The compound of claim 1, wherein
R$^1$ represents an alkyl radical with from 2 to 5 C atoms, a cyclopropylmethyl radical or a methoxyethyl radical, and
R$^2$ represents a 2-(3,4-methylene dioxyphenyl)ethyl radical or a 2-phenyl ethenyl radical substituted with R$^3$, R$^4$ and R$_5$ in positions 3, 4 and 5 on the benzene ring, and wherein, independently of one another,
R$^3$ and R$^5$ are methoxy, and
R$^4$ is a straight-chain or branched alkoxy radical with from 1 to 5 C atoms, an allyloxy radical, a cyclopentyloxy radical, a cyclopropyl methoxy radical or a methoxyethoxy radical.

3. A method of preparing the compound of formula I according to claim 1, in which R$^2$ is a 2-(3,4-methylene dioxyphenyl)ethyl radical, comprising reacting a compound of formula II

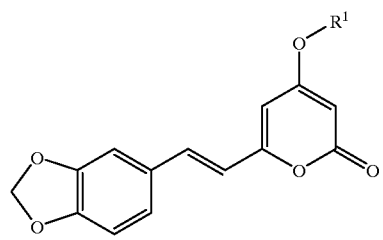

(II)

in which R$^1$ has the meaning set out in claim 1 or 2, with hydrogen in the presence of a catalyst.

4. A reactive intermediate product of formula II in which R$^2$ is a 2-(3,4-methylene dioxyphenyl)ethyl radical,

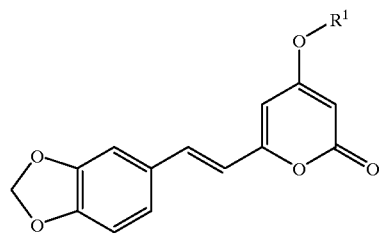

(II)

wherein
R$^1$ represents an alkyl radical with from 2 to 5 C atoms, a cycloalkyl radical with from 4 to 6 C atoms, a cycloalkyl alkyl radical with from 4 to 8 C atoms or an alkoxyalkyl radical with altogether 3 to 5 C atoms.

5. A reactive intermediate product of formula III in which R$^2$ is a 2-phenyl ethenyl radical substituted with R$^3$, R$^4$ and R$^5$ in positions 3, 4 and 5 on the benzene ring, and for preparing the compounds of formula II

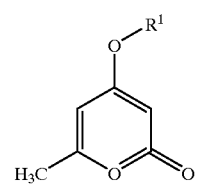

(III)

wherein
R$^1$ represents an alkyl radical with from 3 to 5 C atoms, a cycloalkyl radical with from 4 to 6 C atoms, a cycloalkyl alkyl radical with from 4 to 8 C atoms or an alkoxyalkyl radical with altogether 3 to 5 C atoms.

6. A pharmaceutical composition, containing at least one compound according to claim 1 optionally together with conventional adjuvants and additives.

7. A method of using the compounds of claim 1 for producing a medicament with an anti-convulsive and/or anti-epileptic effect.

8. A method of using the compounds of claim 1 for producing a medicament with a neuro-protective effect and/or with an effect against neuro-degenerative diseases or symptoms.

9. A method of providing an anti-convulsive and/or anti-epileptic effect to a patient in need of such treatment comprising administering to said patient a safe and effective amount of one or more compounds according to claim 1.

10. A method of treating neurodegenerative diseases in a patient in need of such treatment comprising administering to said patient a safe and effective amount of or more compounds according to claim 1.

11. A method of preparing the compound of Formula I:

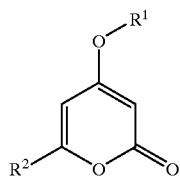
(I)

comprising condensing a pyranone of Formula III, in which $R^1$ represents an alkyl radical with from 2 to 5 C atoms, a cycloalkyl radical with from 4 to 6 C atoms, a cycloalkyl alkyl radical with from 4 to 8 C atoms or an alkoxyalkyl radical with 3 to 5 C atoms, with a benzaldehyde of Formula IV substituted with $R^3$, $R^4$ and $R^5$ in positions 3, 4 and 5, in which $R^3$ and $R^5$ are methoxy or ethoxy, and $R^4$ is a straight chain or branched alkoxy radical with from 1 to 5 C atoms, an alkenyloxy radical with from 3 to 5 C atoms, a cycloalkoxy radical with from 4 to 6 C atoms, a cycloalkyl alkoxy radical with from 4 to 8 C atoms, or an alkoxy alkoxy radical with 3 to 5 C atoms.

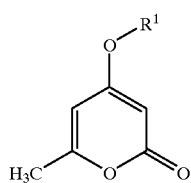
(III)

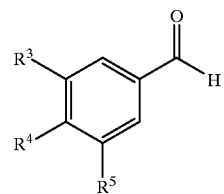
(IV)

12. A method of preparing the compound of Formula II.

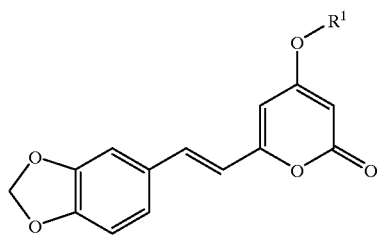
(II)

comprising condensing a pyranone of Formula III in which $R^1$ represents an alkyl radical with from 2 to 5 C atoms, a cycloalkyl radical with from 4 to 6 C atoms, a cycloalkyl alkyl radical with from 4 to 8 C atoms, or an alkoxyalkyl radical with 3 to 5 C atoms, with piperonal.

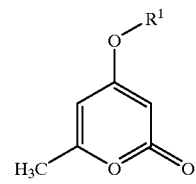
(III)

* * * * *

UNITED STATES PATENT AND TRADEMARK OFFICE
CERTIFICATE OF CORRECTION

PATENT NO. : 6,288,109 B1
DATED : September 11, 2001
INVENTOR(S) : Shyam Sunder Chatterjee & Hermann Hauer Page 1 of 1

It is certified that error appears in the above-identified patent and that said Letters Patent is hereby corrected as shown below:

Column 13,
Line 57, "$R_5$" should read as -- $R^5$ --

Signed and Sealed this

Fifth Day of March, 2002

Attest:

Attesting Officer

JAMES E. ROGAN
*Director of the United States Patent and Trademark Office*